United States Patent [19]

Yoshino et al.

[11] Patent Number: 5,071,982

[45] Date of Patent: Dec. 10, 1991

[54] PROCESS FOR PRODUCING A 4,6-BIS(DIFLUOROMETHOXY)-2-ALKYL-THIOPYRIMIDINE

[75] Inventors: Sumio Yoshino, Fujioka; Kazuyuki Watanabe, Tokyo; Mikio Akazawa, Kawaguchi, all of Japan

[73] Assignees: Asahi Glass Co., Ltd., Tokyo, Japan; Ciba-Geigy AG, Basel, Switzerland; Kawaguchi Chemical Industry Company, Ltd., Tokyo, Japan

[21] Appl. No.: 558,297

[22] Filed: Jul. 26, 1990

[51] Int. Cl.$^5$ .......................................... C07D 239/60
[52] U.S. Cl. ...................................................... 544/303
[58] Field of Search ........................................ 544/303

[56] References Cited

U.S. PATENT DOCUMENTS

| | | | |
|---|---|---|---|
| 4,542,216 | 9/1985 | Pfluger | 544/320 |
| 4,692,524 | 9/1987 | Hassig | 544/303 |
| 4,900,827 | 2/1990 | Seifert et al. | 544/303 |

FOREIGN PATENT DOCUMENTS 0158594  10/1985  European Pat. Off. .

Primary Examiner—John M. Ford
Attorney, Agent, or Firm—Oblon, Spivak, McClelland, Maier & Neustadt

[57] ABSTRACT

A process for producing a 4,6-bis(difluoromethoxy)-2-alkylthiopyrimidine, which comprises reacting a 2-alkylthiobarbituric acid and monochlorodifluoromethane in the presence of a base in an inert solvent, wherein, for a first reaction, after charging a part of the base, the rest of the base and the monochlorodifluoromethane are simultaneously introduced to obtain a mixture of a 4-difluoromethoxy-6-hydroxy-2-alkylthiopyrimidine and a 4,6-bis(difluoromethoxy)-2-alkylthiopyrimidine, and then, for a second reaction, to this mixture, the base and the monochlorodifluoromethane are again simultaneously introduced, or the base is charged first and then the monochlorodifluoromethane is introduced.

6 Claims, No Drawings

PROCESS FOR PRODUCING A 4,6-BIS(DIFLUOROMETHOXY)-2-ALKYLTHIOPYRIMIDINE

BACKGROUND OF THE INVENTION

1. Field of the Invention

The present invention relates to an improved process for producing a 4,6-bis(difluoromethoxy)-2-alkylthiopyrimidine which is useful as an intermediate for agricultural chemicals.

2. Discussion of Background

Heretofore, Japanese Unexamined Patent Publications No. 218378/1985 and No. 281869/1987 have disclosed processes for producing 4,6-bis(difluoromethoxy)-2-methylthiopyrimidine. According to the former process, a base is charged first using dioxane as the solvent for reaction, and then monochlorodifluoromethane and 2-methylthiobarbituric acid are reacted, whereupon the organic layer is separated and recovered, and dioxane is added again to the aqueous phase, and then the mixture is again reacted with the monochlorodifluoromethane, whereupon the organic layer is separated and recovered. This operation is repeated, and then the organic layers are put together, and the desired product is recovered by a usual method. However, the yield of the desired product according to this process is as low as 25%, and therefore, the process can hardly be qualified as an industrial process.

On the other hand, in the latter process, 4-chloro-6-hydroxy-2-methylthiopyrimidine as the starting material is first reacted with monochlorodifluoromethane to obtain 4-chloro-6-difluoromethoxy-2-methylthiopyrimidine, then this product was reacted with sodium nitrite in dimethylformamide t obtain 4-hydroxy-6-difluoromethoxy-2-methylthiopyrimidine, which is further reacted with monochlorodifluoromethane in dioxane in the presence of potassium hydroxide to obtain desired 4,6-bis(difluoromethoxy)-2-methylthiopyrimidine at a yield of 50%. However, this process also involves long process steps and is very cumbersome, and as such, it is not suitable as an industrial process.

SUMMARY OF THE INVENTION

It is an object of the present invention to solve the above problems of the conventional processes.

The present inventors have conducted extensive studies to solve the above-mentioned problems and as a result, have finally accomplished the present invention.

The present invention provides a process for producing a 4,6-bis(difluoromethoxy)-2-alkylthiopyrimidine, which comprises reacting a 2-alkylthiobarbituric acid and monochlorodifluoromethane in the presence of a base in an inert solvent, wherein, for a first reaction, after charging a part of the base, the rest of the base and the monochlorodifluoromethane are simultaneously introduced to obtain a mixture of a 4-difluoromethoxy-6-hydroxy-2-alkylthiopyrimidine and a 4,6-bis(difluoromethoxy)-2-alkylthiopyrimidine, and then, for a second reaction, to this mixture, the base and the monochlorodifluoromethane are again simultaneously introduced, or the base is charged first and then the monochlorodifluoromethane is introduced.

Namely, according to the process of the present invention, it is surprisingly possible to suppress side reactions by reacting the base and the monochlorodifluoromethane in two steps, respectively, at the time of reacting the 2-alkylthiobarbituric acid and the monochlorodifluoromethane in the presence of the base using an inert solvent as the solvent for reaction and to produce the desired 4,6-bis(difluoromethoxy)-2-alkylthiopyrimidine in good yield by relatively short process steps.

Namely, according to the process of the present invention, it is possible to suppress the conversion of the 4,6-bis(difluoromethoxy)-2-alkylthiopyrimidine once formed by the reaction to a by-product by a further reaction with monochlorodifluoromethane.

DETAILED DESCRIPTION OF THE PREFERRED EMBODIMENTS

The inert solvent useful for the process of the present invention includes, for example, formamide, N,N-dimethylformamide, N,N-dimethylacetamide, dimethyl sulfoxide, acetonitrile, diethyl ether, dioxane, tetrahydrofuran, acetone, methyl ethyl ketone, methyl isobutyl ketone, methanol, ethanol and isopropanol. Particularly preferred is dioxane.

As the base useful for the process of the present invention, a hydroxide of an alkali metal such as sodium hydroxide, potassium hydroxide or lithium hydroxide, or a carbonate of an alkali metal such as sodium carbonate or sodium hydrogen carbonate, may be mentioned. Particularly preferred is sodium hydroxide or potassium hydroxide.

In the present invention, the amount of said part of the base charged first for the first reaction is usually from 1.0 to 4.0, preferably from 1.5 to 3.5, by molar ratio to the 2-alkylthiobarbituric acid. If the molar ratio of the base is smaller than this range, the reaction rate tends to decrease, such being undesirable. On the other hand, if it exceeds this range, a side reaction tends to proceed, such being undesirable.

Further, the molar ratio of the base to the 2-alkylthiobarbituric acid for the first reaction is usually within a range of from 5.0 to 10.0, preferably from 6.0 to 8.0. If the molar ratio is less than this range, the reaction rate tends to decrease, and if it exceeds this range, a side reaction tends to take place, such being undesirable.

The molar ratio of the monochlorodifluoromethane to the 2-alkylthiobarbituric acid for the first reaction is usually from 4.0 to 7.0, preferably from 4.5 to 6.5. If the molar ratio is less than this range, the reaction rate and the conversion tend to decrease, and if it exceeds this range, a side reaction tends to proceed, such being undesirable.

In the present invention, the molar ratio of the base to the 2-alkylthiobarbituric acid for the second reaction is usually within a range of from 1.0 to 5.0, preferably from 2.0 to 4.0. If the molar ratio is less than this range, the reaction rate and the conversion tend to decrease, such being undesirable. On the other hand, if it exceeds this range, a side reaction tends to proceed, whereby the yield will be low, such being undesirable.

In the present invention, the molar ratio of the monochlorodifluoromethane to the 2-alkylthiobarbituric acid for the second reaction is usually within a range of from 1.0 to 5.0, preferably from 1.0 to 3.5. If the molar ratio is less than this range, the reaction rate and the conversion tend to decrease, such being undesirable. In the present invention, the reaction temperature for each of the first and second reactions may be selected within a range of from 20° to 100° C., but it is preferably within a range of from 40° to 80° C. in view of the reaction rate and the conversion.

The 2-alkyl group in the 4,6-bis(difluoromethoxy)-2-alkylthiopyrimidine is preferably a lower alkyl group such as 2-methyl, 2-ethyl, 2-propyl or 2-butyl.

Now, the present invention will be described in further detail with reference to Examples. However, it should be understood that the present invention is by no means restricted by such specific Examples.

EXAMPLE 1

Into a four-necked flask equipped with a stirrer, a cooling condenser, a thermometer, a dropping funnel and a gas supply tube, 400 ml of dioxane, 80 ml (0.8 mol) of a 40 V% sodium hydroxide aqueous solution, 60 ml of water and 63.2 g (0.4 mol) of 2-methylthiobarbituric acid, were charged. The internal temperature was raised to 60° C. under stirring to dissolve the content. While maintaining the internal temperature at a level of from 60° to 70° C., 200 ml (2.0 mols) of a 40 V% sodium hydroxide aqueous solution was dropwise added over a period of 4 hours. At this time, 225 g (2.6 mols) of monochlorodifluoromethane was simultaneously introduced in four hours and reacted. Thereafter, the stirring was continued at the same temperature for further 30 minutes. The reaction product thereby obtained was adjusted to a pH of about 6 by dropwise adding 30 V% sulfuric acid. Then, an inorganic salt formed by neutralization was removed by filtration. From the filtrate separated into two layers, the dioxane layer was separated and recovered. Then, the aqueous layer was extracted with 300 ml of fresh dioxane, and the extract was combined to the previous dioxane layer. The combined dioxane layer was charged into a reactor equipped with the same apparatus. Then, 80 ml (0.8 mol) of a 40 V% sodium hydroxide aqueous solution was added again. The internal temperature was raised to a level of from 60° to 70° C., and while maintaining the temperature at the same level, 52 g (0.6 mol) of monochlorodifluoromethane was again introduced over a period of 1 hour and reacted. Thereafter, a formed inorganic salt was filtered off. From the filtrate, the dioxane layer was separated by liquid separation. Dioxane was removed from the obtained dioxane layer by distillation, and a yellow oil layer thereby obtained was washed with 100 ml of warm water of about 50° C. This yellow oil layer was distilled under reduced pressure (bp: 104°–109° C./70 mmHg) to obtain 59.5 g of desired 4,6-bis(difluoromethoxy)-2-methylthiopyrimidine. This corresponds to a yield of 57.7% relative to the 2-methylthiobarbituric acid used. When left to stand, this product turned into white crystals, and the melting point was from 47° to 49.5° C.

EXAMPLE 2

The operation was conducted in the same manner as in Example 1 except that the first added 40 V% sodium hydroxide aqueous solution was changed to 40 ml, whereby 55.2 g of 4,6-bis(difluoromethoxy)-2-methylthiopyrimidine was obtained. This corresponds to a yield of 53.5% relative to the 2-methylthiobarbituric acid used, and the melting point was from 47° to 49.5° C.

EXAMPLE 3

The operation was conducted in the same manner as in Example 1 except that the reaction temperature was changed to from 50° to 60° C., whereby 52.6 g of 4,6-bis(difluoromethoxy)-2-methylthiopyrimidine was obtained. This corresponds to a yield of 51.0% relative to the 2-methylthiobarbituric acid used. The melting point of this product was from 46.5° to 49.5° C.

EXAMPLE 4

The operation was conducted in the same manner as in Example 1 except that the reaction temperature was changed to from 70° to 80° C., whereby 50.0 g of 4,6-bis(difluoromethoxy)-2-methylthiopyrimidine having a melting point of from 45.5° to 48.5° C. was obtained. This corresponds to a yield of 48.4% relative to the 2-methylthiobarbituric acid used.

COMPARATIVE EXAMPLE

Into the same apparatus for reaction as used in Example 1, 1,000 ml of dioxane, 763 ml (7.63 mols) of a 40 V% sodium hydroxide aqueous solution and 130 g (0.82 mol) of 2-methylthiobarbituric acid were charged and heated to dissolve the content. Then, while maintaining the temperature at a level of from 75° to 80° C., 154 g (1.78 mols) of monochlorodifluoromethane was introduced and reacted. From the reaction solution, the dioxane layer was separated. To the aqueous layer, 1,000 ml of dioxane was added afresh, and 154 g of monochlorodifluoromethane was again introduced and reacted thereto. Then, the dioxane layer was separated and combined to the previous dioxane layer. The combined layer was concentrated and dioxane was removed to obtain 59 g of a yellowish white paste. This product was washed with warm water and distilled under reduced pressure to obtain 39.5 g of an oily substance. This corresponds to a yield of 18.7% relative to the 2-methylthiobarbituric acid used. This product was crystallized to obtain white crystals having a melting point of from 47° to 49° C.

According to the present invention, a side reaction can be suppressed, and it is possible to produce a 4,6-bis(difluoromethoxy)-2-alkylthiopyrimidine in relatively short process steps and in good yield, which can not be attained by the conventional processes.

What is claimed is:

1. A process for producing a 4,6-bis(difluoromethoxy)-2-alkylthiopyrimidine, which comprises reacting a 2-alkylthiobarbituric acid and monochlorodifluoromethane in the presence of a base in an inert solvent, wherein, for a first reaction, after charging a part of the base, the rest of the base and the monochlorodifluoromethane are simultaneously introduced to obtain a mixture of a 4-difluoromethoxy-6-hydroxy-2-alkylthiopyrimidine and a 4,6-bis(difluoromethoxy)-2-alkylthiopyrimidine, and then, for a second reaction, to this mixture, the base and the monochlorodifluoromethane are again simultaneously introduced, or the base is charged first and then the monochlorodifluoromethane is introduced.

2. The process according to claim 1, wherein the base is sodium hydroxide or potassium hydroxide.

3. The process according to claim 1, wherein the molar ratio of said part of the base charged first, relative to the 2-methylthiobarbituric acid for the first reaction is within a range of from 1.0 to 4.0.

4. The process according to claim 1, wherein the molar ratios of the base and the monochlorodifluoromethane, relative to the 2-methylthiobarbituric acid for the first reaction, are from 5.0 to 10.0 and from 4.0 to 7.0, respectively.

5. The process according to claim 1, wherein the molar ratios of the base and the monochlorodifluoromethane, relative to the 2-methylthiobarbituric acid for the second reaction, are within the ranges of from 1.0 to 5.0 and from 1.0 to 5.0, respectively.

6. The process according to claim 1, wherein the reaction temperature in each of the first and second reactions is within a range of from 20° to 100° C.

* * * * *